United States Patent [19]

Bruce

[11] Patent Number: 5,301,006
[45] Date of Patent: Apr. 5, 1994

[54] EMISSION MICROSCOPE

[75] Inventor: Victoria J. Bruce, Austin, Tex.

[73] Assignee: Advanced Micro Devices, Inc., Sunnyvale, Calif.

[21] Appl. No.: 826,992

[22] Filed: Jan. 28, 1992

[51] Int. Cl.⁵ .................. G01J 3/443; G01N 21/62
[52] U.S. Cl. ................ 356/311; 356/328; 356/417; 356/418
[58] Field of Search ............... 356/311, 317, 318, 326, 356/328, 417, 418, 237; 358/101, 106

[56] References Cited

U.S. PATENT DOCUMENTS 5,166,755 11/1992 Gat ....................... 356/419

Primary Examiner—F. L. Evans
Attorney, Agent, or Firm—Johnson & Gibbs

[57] ABSTRACT

An emission microscope system includes in various embodiments a catadioptric optical microscope and/or a computer automated optical dispensing system and/or a cryogenically cooled back thinned CCD camera. The system also includes a computer controlled data acquisition system with specially tailored software.

9 Claims, 1 Drawing Sheet

EMISSION MICROSCOPE

CROSS REFERENCE TO A RELATED APPLICATION

This application is related to co-pending U.S. patent application Ser. No. 07/827,732 entitled ENERGY RESOLVED EMISSION MICROSCOPY SYSTEM AND METHOD, which was filed on Jan. 29, 1992, which has been assigned to the assignee of the present invention, and which is hereby incorporated herein in its entirety by this reference thereto.

BACKGROUND OF THE INVENTION

1. Field of the Invention

The present invention relates to emission microscopy and, more particularly, to integrated circuit inspection systems.

2. Description of Related Art

In the design of semiconductor devices, including integrated circuits (IC's) and the like, it is often desired to analyze current flow through various circuits. Such analysis can, for example, be undertaken to isolate points of potential failure.

Several types of analysis of current flow through circuits take advantage of the electroluminescent characteristics of silicon. It is well known, for example, that a semiconductor device will, under excitation, emit a small amount of light. Whole electron pairs associated with various defects recombine, and in that process emit photons. Avalanche breakdown, in particular, can be analyzed by observing emitted light. Light emission in an avalanche breakdown situation enables the detection and location of areas of current flow. Oxide defects also can be detected by observing the light emitted upon application of current. By observing the emitted light, the points of failure of a damaged product can be determined, and an analysis of design flaws and/or processing flaws can be undertaken.

All of the foregoing is discussed in greater detail in U.S. Pat. No. 4,680,635. Also discussed in that patent is the use of light emissions to determine the profile and detailed effects of an ESD (electrostatic discharge) event in an integrated circuit. During ESD, p-n junctions become forward biased or even go into avalanche breakdown. Light is emitted in either case. By capturing details regarding the emitted light pattern, aspects of the ESD event can be observed and the area of dissipation of the ESD energy determined.

Study of light emitted by semiconductor devices is rendered somewhat difficult because of the small amounts of light involved. Only about 0.01% of the whole electron pairs in silicon recombine by emitting a photon. Thus, hundreds of milliamperes of current must be applied to a silicon device in avalanche breakdown to view light emitted with the naked, human eye. As application of such high currents is generally not feasible, or ultimately productive, other methods of capturing information regarding emitted light have been developed. Heretofore, for example, light emitted from integrated circuits has been recorded with time exposure photography. A shortcoming of this method, discussed in U.S. Pat. No. 4,680,635, is inability to isolate time as a factor in the light emission. That is to say, steady state conditions, but not transient conditions, can be observed by this method. Accordingly, failure mechanisms that can only be observed in the transient state, such as the hot electron effect in inverters, cannot be observed.

Also in the past light emissions from integrated circuits have been observed using infrared or optical microscopes. Shortcomings of such microscopes for this use are inability to resolve time varying effects (as discussed in the immediately preceding paragraph) and inability to detect faint and/or subtle contrasts in light emissions.

A third past method for observing light emission involves emission microscopes. Prior art details regarding such microscopes, as well as further information regarding the other analysis techniques discussed above in this description of related art section, may be found in the related case, as well as in U.S. Pat. Nos. 4,680,635, 4,755,874, and 4,811,090.

Prior art emission microscope systems, like the other past methods for analyzing circuits based upon light emissions, have a number of shortcomings and deficiencies. For example, the standard grade optical microscopes within prior art systems are not able to transmit light from the near ultraviolet to the infrared without a more than minimal loss of intensity. Although prior systems generally include filter wheels, these filter wheels are not automated and thus are not capable of "stepping through" each filter sequentially to accumulate a spectral graph. Prior art systems also suffer because of poor signal to noise ratios. The combination of an image intensifier and an electronically cooled CCD camera in prior art systems does not have the best quantum efficiency over a broad range of wavelengths presently attainable. Additionally, such a combination has a relatively poor signal to noise ratio. A number of other shortcomings of prior art systems are discussed in the related case.

Based upon all of the foregoing, it should be appreciated that prior art circuit inspection systems, even those incorporating state of the art emission microscopes, have a number of shortcomings and deficiencies that reduce their usefulness.

SUMMARY OF THE INVENTION

The present invention overcomes the shortcomings and deficiencies discussed above by providing an improved emission microscope system. This improved emission microscope system includes a catadioptric optical microscope, a computer automated optical dispersing system, a cryogenically cooled back thinned CCD camera, and improved data acquisition software (discussed in detail in the case related hereto).

More specifically, one embodiment of the present invention is an emission microscope system including an optical subsystem, an intensifier subsystem, a camera subsystem, and a processing subsystem. The optical subsystem comprises a catadioptric optical microscope and, in operation, outputs an optical image. The intensifier subsystem is coupled to the optical subsystem and intensifies the optical image and, in operation, outputs an intensified image. The camera subsystem is coupled to the intensifier subsystem and operates to convert the intensified image to an electronic image signal. The processing subsystem, which is coupled to the camera subsystem, removes noise from the electronic image signal and enhances the electronic image signal.

In embodiments of the present invention the camera subsystem comprises a cryogenically cooled back thinned CCD camera. Also in certain embodiments of the present invention the optical subsystem comprises a computer automated optical dispersing instrument such as an automated motorized filter wheel or an automated dual grating monochromator.

Accordingly, it is an object of the present invention to provide an improved emission microscope system.

Another object of the present invention is to provide a circuit diagnostic tool capable of readily providing photon intensity versus wavelength to yield physical information on hot carriers.

Still yet another object of the present invention is to provide a expedient means to effect failure analysis and reliability evaluation of hot carrier degradation.

BRIEF DESCRIPTION OF THE DRAWINGS

Other objects, advantages, and novel features of the present invention will become apparent from the following detailed description of the invention when considered in conjunction with the accompanying drawings in which.

DETAILED DESCRIPTION OF THE INVENTION

Figure 1:
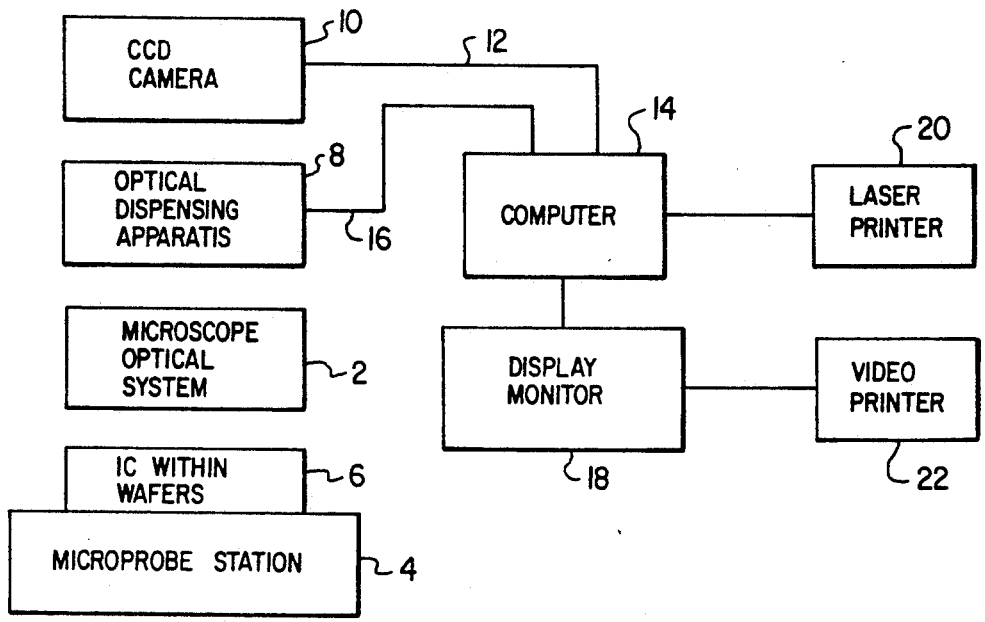
FIG. 1 is a block diagram of an improved emission microscope according to the teachings of the present invention.

Based upon the description of related art section above, it should be appreciated that energy resolved emission microscopy (EREM) is a diagnostic technique which provides a nondestructive method of determining, for example, which of a multitude of transistors within a device have been weakened by hot electron degradation. As another example, EREM provides a method of gaining insight into oxide conduction mechanisms. Additionally, EREM may also be used to distinguish between reverse and forward biased p-n junctions for diagnostic purposes.

Further based upon the information set forth in the description of related art section above, it should be appreciated that EREM involves the spectral analysis of photons emitted from operating VLSI circuitry. ERE utilizes the fact that the energy state of the channel hot electrons may be approximated by a Maxwell-Boltzmann distribution. Since the spectral distribution of the emitted photon energy reflects the energy of the generating carriers, the photon spectra may be approximated by a Maxwell-Boltzmann distribution as well.

Those skilled in the art presently recognize that the intensity of the photon emission at roughly 200 nm correlates directly to the amount of degradation of the transconductance of the device. Thus, those transistors emitting a large number of visible and near ultraviolet photons at the drain edge are undergoing more severe hot electron degradation. Standard grade microscope optics currently found on state of the art emission microscopes, however, do not transmit ultraviolet radiation. In addition, actual analysis of the low intensity 200 nm photon emission requires long CCD exposure times. Due to the poor signal to noise ratio of the electronically cooled CCD camera and photocathode systems, long exposure times are not possible with the state of the art emission microscope systems.

EREM provides two approaches to obtaining the intensity of the 200 nm photon emission. First, the intensity of the 200 nm photon emission may be measured with the catadioptric microscope, the cryogenically cooled back thinned CCD camera and a long exposure time. Second, the intensity of the 200 nm photon emission may be mathematically estimated from the intensity measured in the visible region using the assumption of a Maxwell-Boltzmann distribution.

The experimental procedure of EREM includes the use of a standard hot electron injection (HEI) stress and test procedure. Both the change in transconductance (or $I_{DSAT}$) and the photon intensity at various wavelengths are plotted against the gate voltage. The gate voltage at which the 200 nm photon intensity is the greatest should correlate to the gate voltage at which the change in transconductance is also the greatest. By plotting the spectral energy against the log of the intensity for each gate voltage at a constant drain voltage, unknown variables in the Maxwell-Boltzmann distribution function for a particular device may be determined. Once these unknown variables are determined, an estimate of the intensity at 200 nm may be easily obtained.

A computer may provide complete automation of the data acquisition process. The data may be automatically corrected for the spectral response of the entire system and displayed graphically in a plot of wavelength versus intensity. The computer may be interfaced with a parametric analyzer for plots of wavelength versus intensity versus voltage. For hot electron analysis, the intensity of the emission at 200 nm and an estimate of device lifetime may be obtained.

A system including software according to the teachings of the present invention and the teachings in the related case may also encompass the image processing benefits of state of the art emission microscopes for oxide defects and ESD energy dissipation events. Characteristic spectra may be obtained for various failure mechanisms and may be stored on file and recalled for comparison to spectra obtained from integrated circuitry under analysis.

Referring now to the drawings wherein like reference numerals are used to designate similar or identical elements throughout the several views and, more particularly, to FIG. 1, there is shown in block diagram form an energy resolved emission microscope (EREM) that may be used to analyze the spectral content of electroluminescence from biased semiconductor devices. The present invention consists of a series of improvements designed to enhance the spectral sensitivity and automate the spectral acquisition process of state of the art emission microscopes. The present invention comprises a microscope optical system 2 operatively coupled to, i.e., focused on, a microprobe station 4. The microprobe station 4 allows the flexibility of analyzing integrated circuitry within wafers, individual die or packaged devices or the like 6. A stimulating current is supplied to the circuitry via conventional probe cards, external pins microprobes or the like (not shown in FIG. The microscope optical system 2 may then be used to view the emitting circuitry. The system 2 comprises a standard optical microscope with objectives and standard grade glass and/or acrylic lenses. Alternatively, system 2 may comprise a catadioptric optical microscope with a corrector lens made with high grade fused silica glass. The catadioptric optical microscope alternative is preferred because it permits high efficiency transmission of a broad range of wavelengths from the near ultraviolet to the infrared. To transmit wavelengths shorter than the near ultraviolet (<200 nm), the system must be purged with an inert gas or encased in a vacuum.

The image produced by the microscope Optical (system passes through an optical dispersing apparatus 8. The optical dispersing apparatus 8 ideally includes a high throughput dual grating monochromator which allows spectral dispersion and analysis of emitted light in a single acquisition. As an alternative the optical dispersing apparatus 8 may comprise a motorized filter wheel containing a variety of narrowband interference filters for repeated extraction of radiation in narrow spectral ranges.

The output of the optical dispersing apparatus 8 is operatively coupled to a camera subsystem, most preferably a back thinned cryogenically cooled photon counting CCD camera 10. The operative coupling of the apparatus 8 and camera 10 effectively comprises the latter being focused through the former so that a device being analyzed 6 is photographed by the camera 10 through the apparatus 8 and the system 2. A back thinned cryogenically cooled CCD camera 10 provides increased sensitivity in detecting photon emissions because of its high quantum efficiency and low noise level. The output signal of the CCD camera is coupled (this coupling shown by line 12 in FIG. 1) to a computer 14 for image processing and for analysis of the spectral data. The software designed specifically to analyze the data and to determine the failure mode and the amount of hot electron degradation is described in detail in the application related hereto identified above. The entire data acquisition process including the operation of the camera and the automation of the monochromator and/or filter wheel to step through the entire range of wavelengths selected is controlled by the computer 12. Computer control is exerted on the optical dispensing apparatus via line 16 shown in FIG.

Computer 14 is also coupled to a high resolution display monitor 18 and to a laser printer 20 for outputting hard copies of the computer enhanced images and the spectral data. The monitor 18 outputs a standard RS170 signal which may be coupled to a video printer 22.

Based upon the foregoing, those skilled in the art should appreciate that a number of significant improvements to emission microscope systems are described herein.

Figure 2:
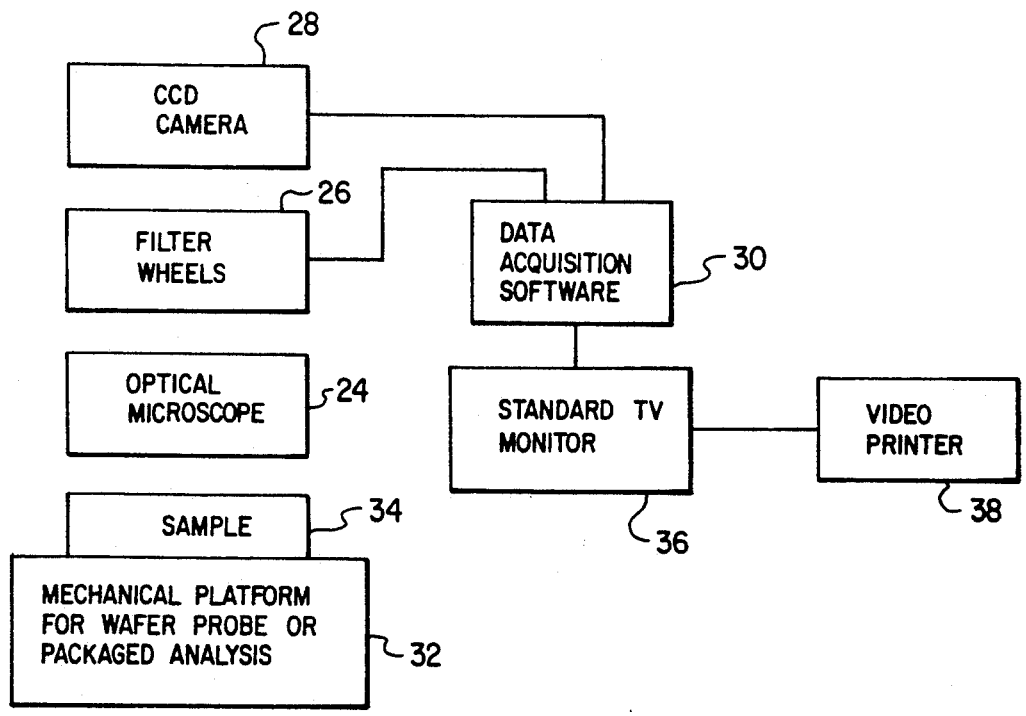
FIG. 2 is block diagram of an prior art emission microscope compared to which the present invention includes and offers significant improvements.

First, replacement of the standard grade optical microscopes shown in FIG. 2 as element 24 found on state of the art systems with a catadioptric optical microscope (element 2 in FIG. 1) is such an improvement. The catadioptric optical microscope transmits light from the near ultraviolet to the infrared with minimal loss of intensity.

A second improvement involves the addition of a computer automated optical dispersing instrument (element 8 in FIG. 1) which may be either a fully automated motorized filter wheel to sequentially step through each of a series of narrow band interference filters for accumulation of photon counts per wavelength without user interaction or a fully automated dual grating monochromator with output port for mounting a CCD camera head. The motorized filter wheel allows the data acquisition process to execute expediently. The dual grating monochromator provides increased wavelength resolution and simultaneous intensity measurement of all wavelengths. Although the current state of the art systems include filter wheels (see element 2 in FIG. 2), these filter wheels 26 are not fully automated and do not step through each filter sequentially to accumulate a spectral graph.

A third improvement involves replacement of the state of the art image intensifier and electronically cooled CCD camera system (element 28 in FIG. 2) with a cryogenically cooled back thinned CCD camera (element 10 in FIG. 1). The cryogenically cooled back thinned CCD camera provides an increased quantum efficiency over a broader range of wavelengths, as well as a larger signal to noise level. The current state of the art emission microscopes are severely limited in photon counting by their poor signal to noise ratio.

Still further, improvements are made in embodiments of the present invention to FIG. data acquisition software used within computer 14 in FIG. 1. These improvements are discussed at length in the related case. These improvements include correcting the acquired photon counts for the spectral response of the entire system. The correction factors are obtained by calibrating the system with a light source of known intensity and spectral distribution. The software improvements also include full automation of the optical dispersion apparatus and graphical display of the spectral data corrected for system response. The computer also acquires data from a parametric analyzer or other electronic characterization apparatus. This data is displayed graphically against the spectral data in a three dimensional plot. A data analysis routine approximates the extent of the hot electron degradation, as well as the device lifetime. The improvements also include enhanced image processing software. Thus, the software used in computer 14 in embodiments of the present invention is significantly better than data acquisition software 30 (in FIG. 2) in prior art systems.

Continuing to refer to FIG. 2, a platform 32, sample 34, monitor 36, and printer 38 are shown to present a complete prior art system; these elements are not significantly different from the elements shown in FIG. 1 although better information can be expected to be provided via monitor 18 and printer 22 for reasons previously discussed.

Based upon the foregoing, those skilled in the art should now fully appreciate the structure and use of the present invention. The present invention provides an energy resolved emission microscope system that can be readily used to analyze the spectral content of electroluminescence from biased semiconductor devices. The present invention comprises a series of improvements designed to enhance the spectral sensitivity and to automate the spectral acquisition process of state of the art emission microscopes.

Those skilled in the art will recognize that many modifications and variations besides those specifically mentioned ma be made in the structure and techniques described herein without departing from the concept of the present invention. Accordingly, it should be understood that, within the scope of the appended claims, the present invention may be practiced otherwise than as specifically described herein.

What is claimed is:

1. An emission microscope system comprising:
   an optical subsystem, said optical subsystem comprising a catadioptric optical microscope, said optical subsystem outputting an optical image;
   a computer automated optical dispersing subsystem for varying wavelengths during which photons may be counted, said computer automated optical dispersing subsystem positioned relative to said optical subsystem so that said optical image output by said optical subsystem passes through said computer automated optical dispersing subsystem;

a camera subsystem focused upon said optical image output by said optical subsystem and passing through said computer automated optical dispersing subsystem, said camera subsystem converting said optical image to an electronic image signal; and a processing subsystem operatively coupled to said camera subsystem and to said computer automated optical dispersing subsystem for controlling them and for acquiring and manipulating data obtained therefrom.

2. A system as recited in claim 1, wherein said camera subsystem comprises a cryogenically cooled back thinned CCD camera.

3. A system as recited in claim 1, wherein said computer automated optical dispersing subsystem comprises an automated motorized filter wheel.

4. A system as recited in claim 1, wherein said computer automated optical dispersing system further comprises an automated dual grating monochromator.

5. A device for magnifying and displaying output images of light emitted from semiconductor devices as a result of electrical stimulation, said device comprising:

optical means for viewing said semiconductor device, said optical means outputting an optical image;

a cryogenically cooled back thinned CCD camera means positioned relative to said optical means so that said optical image output by said optical means is received by said camera means, said camera means acting to convert said optical image to an electronic image signal; and processing means coupled to said camera means for removing noise from said electronic image signal and for enhancing said electronic image signal, said processing means outputting an enhanced image signal.

6. A device as recited in claim 5, wherein said optical means comprises a catadioptric optical microscope.

7. A device as recited in claim 6, wherein said optical means further comprises a computer automated optical dispersing instrument.

8. A system as recited in claim 7, wherein said computer automated optical dispersing instrument comprises an automated motorized filter wheel.

9. A system as recited in claim 8, wherein said computer automated optical dispersing instrument comprises an automated dual grating monochromator.

* * * * *